United States Patent
Ramachandran et al.

(10) Patent No.: US 8,736,831 B2
(45) Date of Patent: May 27, 2014

(54) SUBSTRATE INSPECTION

(75) Inventors: Mahendra Prabhu Ramachandran, Palo Alto, CA (US); Steven W. Meeks, Palo Alto, CA (US); Romain Sappey, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 13/472,421

(22) Filed: May 15, 2012

(65) Prior Publication Data

US 2013/0308124 A1    Nov. 21, 2013

(51) Int. Cl.
*G01N 21/00*     (2006.01)
*G01N 21/95*     (2006.01)
*G01N 21/956*    (2006.01)

(52) U.S. Cl.
CPC .......... *G01N 21/9501* (2013.01); *G01N 21/956* (2013.01)
USPC ................ 356/237.2; 356/237.1; 356/237.3; 356/237.4

(58) Field of Classification Search
CPC .......................... G01N 21/9501; G01N 21/956
USPC ............... 356/237.1–237.5, 394; 250/559.45, 250/559.4, 559.46
See application file for complete search history.

(56) References Cited

U.S. PATENT DOCUMENTS

| | | | |
|---|---|---|---|
| 5,506,676 A * | 4/1996 | Hendler et al. | 356/237.1 |
| 5,539,213 A | 7/1996 | Meeks et al. | |
| 5,586,040 A | 12/1996 | Baumgart et al. | |
| 6,392,748 B1 * | 5/2002 | Fateley | 356/330 |
| 6,486,946 B1 | 11/2002 | Stover et al. | |
| 6,538,730 B2 | 3/2003 | Vaez-Iravani et al. | |
| 6,643,007 B2 * | 11/2003 | Le | 356/237.3 |
| 6,686,602 B2 * | 2/2004 | Some | 250/559.45 |
| 7,116,413 B2 | 10/2006 | Vaez-Iravani | |
| 7,330,265 B2 * | 2/2008 | Kurosawa et al. | 356/445 |
| 7,492,451 B2 | 2/2009 | Vaez-Iravani et al. | |
| 7,535,563 B1 | 5/2009 | Chen et al. | |
| 7,554,654 B2 | 6/2009 | Meeks et al. | |
| 7,562,057 B2 * | 7/2009 | Maggioni et al. | 706/20 |
| 7,697,128 B2 * | 4/2010 | Snel et al. | 356/237.5 |
| 7,907,269 B2 | 3/2011 | Meeks | |
| 8,018,586 B2 * | 9/2011 | Genio et al. | 356/237.2 |
| 2004/0085533 A1 | 5/2004 | Fossey et al. | |

\* cited by examiner

*Primary Examiner* — Sang Nguyen
(74) *Attorney, Agent, or Firm* — Ann Marie Mewherter

(57) ABSTRACT

Various embodiments for substrate inspection are provided.

26 Claims, 8 Drawing Sheets

SUBSTRATE INSPECTION

STATEMENT REGARDING FEDERALLY SPONSORED RESEARCH OR DEVELOPMENT

The U.S. Government has certain rights in one or more claims of this invention as provided for by the terms of Contract No. DE-EE0003159 awarded by the Department of Energy—Falcon Program.

BACKGROUND OF THE INVENTION

1. Field of the Invention

The present invention generally relates to substrate inspection.

2. Description of the Related Art

The following description and examples are not admitted to be prior art by virtue of their inclusion in this section.

Transparent substrates such as silicon carbide and sapphire are frequently used in the fabrication of light emitting diodes (LEDs). Such transparent substrates are often polished on only a single side of the substrate. For example, the upper active surface is polished and the lower inactive surface remains unpolished. The upper active surface may also be patterned with voids or bumps.

It can be difficult to inspect the polished upper surface of the substrates described above and any transparent films formed thereon. For example, a light beam used by an inspection system will penetrate the transparent substrate and strike the bottom unpolished surface. Scattered light from the bottom unpolished surface can be collected and detected by the inspection system along with other scattered light that is desired to be detected. As a result, the scattered light signal from the unpolished bottom surface typically overwhelms the signal from the defects on the top surface and any transparent films formed thereon. In addition, in the case of a patterned substrate, the light will scatter from patterned structures formed on the upper active surface and that signal will be superimposed on the signal from the defects on the top surface and any transparent films formed thereon. Therefore, it can be difficult to detect any defects that might be present on the top surface of the substrate or in or on any transparent material formed thereon.

Accordingly, it would be advantageous to develop methods and systems for substrate inspection that do not have one or more of the disadvantages described above.

SUMMARY OF THE INVENTION

The following description of various embodiments is not to be construed in any way as limiting the subject matter of the appended claims.

An embodiment relates to a system configured to inspect a substrate. The system includes an illumination subsystem configured to direct light to the substrate. Patterned features are formed on an upper surface of the substrate. The system also includes an objective configured to collect light scattered from the substrate. In addition, the system includes an optical element positioned in a path of the light collected by the objective. The optical element is configured to direct light scattered from the patterned features into a first direction and other scattered light into a second direction. The system further includes a detector configured to generate output responsive to only the light directed into the second direction. The system also includes a processor configured to detect defects on the substrate using the output. The system may be further configured according to any embodiment(s) described herein.

Another embodiment relates to a system configured to inspect a substrate. The system includes an illumination subsystem configured to direct light to the substrate. Patterned features are formed on an upper surface of the substrate. The system also includes an objective configured to collect light scattered from the substrate, in addition, the system includes an optical element positioned in a path of the light collected by the objective. The optical element is configured to direct light scattered from the patterned features into a first direction and other scattered light into a second direction. The system further includes a first detector configured to generate output responsive to only the light directed into the second direction and a second detector configured to generate output responsive to only the light directed into the first direction. The system also includes a processor configured to detect defects in the patterned features or to determine one or more characteristics of the patterned features using the output generated by the second detector. The system may be further configured according to any embodiment(s) described herein.

An additional embodiment relates to a system configured to inspect a substrate. The system includes an illumination subsystem configured to direct light to the substrate. Patterned features are not formed on an upper surface of the substrate. The system also includes an objective configured to collect light scattered from the substrate. In addition, the system includes an optical element positioned in a path of the light collected by the objective. The optical element is configured to selectively direct the collected light into a first direction or a second direction. The system further includes a detector configured to generate output responsive to only the light directed into the second direction. The system also includes a processor configured to detect defects on the substrate using the output. During inspection of the substrate, the optical element is configured to direct all of the collected light into the second direction. The system may be further configured according to any embodiment(s) described herein.

In some embodiments, the systems described herein may be used for defect review. For example, the optical element may be used for a detailed review or classification improvement of defects detected on the other substrate. Alternatively, the optical element may be replaced with a detector that may be used for defect review and classification. The optical element or the detector may be used to sample different portions of the scattered light to determine differential scattering cross-section of a defect and this information can be used to classify the defect.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
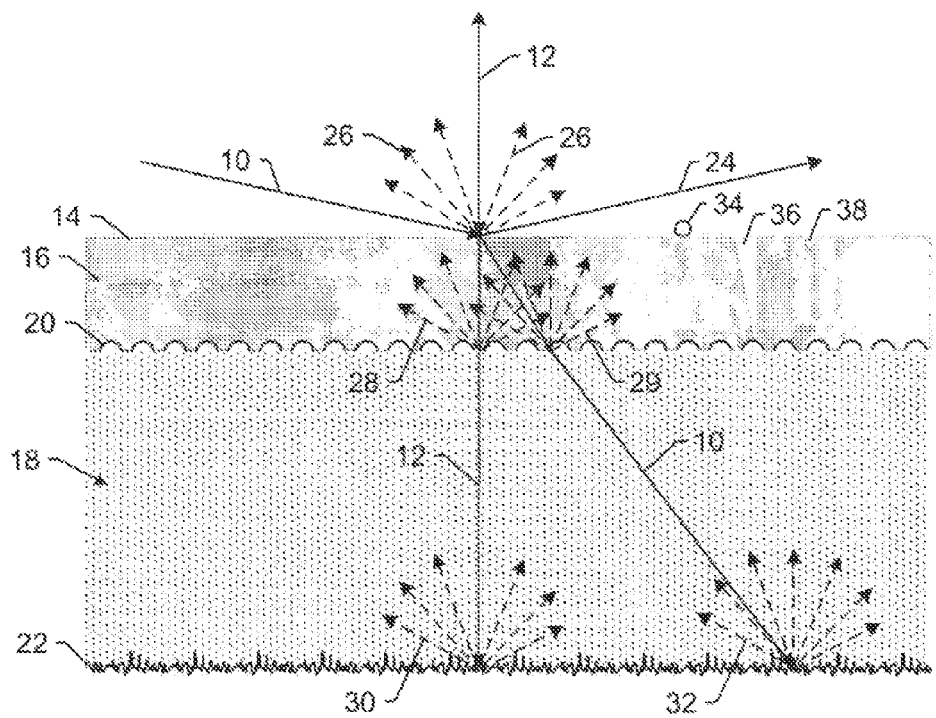
FIG. 1 is a schematic diagram illustrating a cross-sectional view of one example of a patterned transparent substrate and various scattered light from different portions of the patterned transparent substrate as a result of illumination.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

As used herein, the term "substrate" refers to a substrate that may or may not have one or more layers formed thereon and/or may or may not have one or more periodic patterns, either topographic (e.g., bumps) or material based (e.g., metal filled trenches on top of a semiconductor or dielectric sample). In addition, "patterned features" as used herein may include topographic or material based patterns. The "patterned features" may also be other and/or aperiodic features on the substrate such as nuisance defects (e.g., nuisance defects called "fish-scale" defects on account of their relatively smooth shape) or other features that are not intentionally formed on the substrate. Such "patterned" features may have substantially low spatial frequencies (e.g., much lower than the spatial frequencies of typical patterned device features).

Some embodiments described herein may be used for patterned sapphire substrates (PSS) based light emitting diode (LED) wafer inspection. PSS are becoming increasingly common in the LED industry as they offer benefits in light extraction efficiency for a certain type of final device process. Gallium nitride (GaN) may be grown via an epitaxial process on PSS. The pattern may include micron size bumps or voids that are placed at 1 to 3 micron periods. The bumps or voids are produced on the sapphire surface via a lithographic process. The size, shape, and period of the bumps or voids can vary widely. The symmetry of the bumps or voids may be hexagonal, so as to match the symmetry of the GaN crystal.

The presence of periodic bumps or voids creates a problem when one tries to inspect the GaN for defects using scattered visible light. In particular, the visible light will pass through the GaN and scatter from the PSS and from the unpolished backside of the wafer. One way to avoid this would be to use a wavelength of light where the GaN is opaque (wavelengths less than 365 nm), but many defects in the GaN epi layer lie within or beneath the epitaxial layer, and as a result using a wavelength where GaN is opaque would prevent detection of these defects.

A solution to separating the top and bottom surface scattered light for an unpatterned sapphire wafer is given in commonly owned U.S. Pat. No. 7,907,269 to Meeks, which is incorporated by reference as if fully set forth herein. The embodiments described herein extend the technology described in this patent to the case of separating the GaN scattered light, the PSS scatter, and the bottom surface scatter. The embodiments described herein may also be configured as described in U.S. Pat. No. U.S. Pat. No. 6,486,946 to Stover et al., U.S. Pat. No. 7,535,563 to Chen et al., and U.S. Pat. No. 7,907,269 to Meeks and U.S. Patent Application Publication No. 2004/0085533 to Fossey et al., all of which are incorporated by reference as if fully set forth herein.

FIG. 1 shows the case of two light beams 10 and 12 striking top surface 14 of GaN 16 on PSS 18. The light beams may include two visible beams. For example, one light beam may be in the red spectrum (e.g., 660 nm) and the other light beam may be in the violet spectrum (e.g., 405 nm). The wavelengths of the light beams may vary depending on the composition of the transparent material and the substrate. In addition, the angles of incidence at which the light beams are directed to the substrate may vary depending on the composition of the transparent material and the substrate. Furthermore, the two light beams may be directed to the substrate at different angles of incidence (e.g., one beam at a normal or near normal angle of incidence and the other at an oblique angle of incidence such as 70 degrees). As shown in FIG. 1, the PSS includes patterned features 20 formed on an upper surface of the substrate. In addition, bottom surface 22 of the substrate is typically not polished and therefore may have substantial roughness compared to other surfaces of the substrate and transparent material. It should also be clear that the embodiments described herein are applicable to the case where only one beam is used, or more than 2 beams are used.

The scattered light from the individual surfaces and interfaces is indicated in FIG. 1. For example, as shown in FIG. 1, light beam 10 may be specularly reflected from the upper surface of the GaN as reflected beam 24. In addition, light beams 10 and 12 may be scattered from the upper surface of the GaN as scattered light 26. Light beam 12 may penetrate the GaN layer and be scattered from the upper surface of the transparent substrate and the patterned features as scattered light 28. In addition, light beam 12 may penetrate the substrate and be scattered from the bottom surface of the substrate as scattered light 30. Light beam 10 may penetrate the GaN surface and scatter from the upper surface of the transparent substrate and the patterned features as scattered light 29. Light beam 10 may also penetrate the substrate and be scattered from the bottom surface as scattered light 32. The scattered light contains information about defects on, within, and below the GaN surface. Such defects may include, for example, particle 34, microcrack 36, and micropit 38, which may have a diameter of about 0.1 um to about 1 um. To enable or improve defect detection capability, it is desired to separate this scatter from the GaN from 1) the scattered tight from the PSS and 2) bottom surface scatter. In the case of a patterned opaque substrate, the substrate may be silicon on which LEDs may be grown as well as with or without it being patterned.

Figure 2:
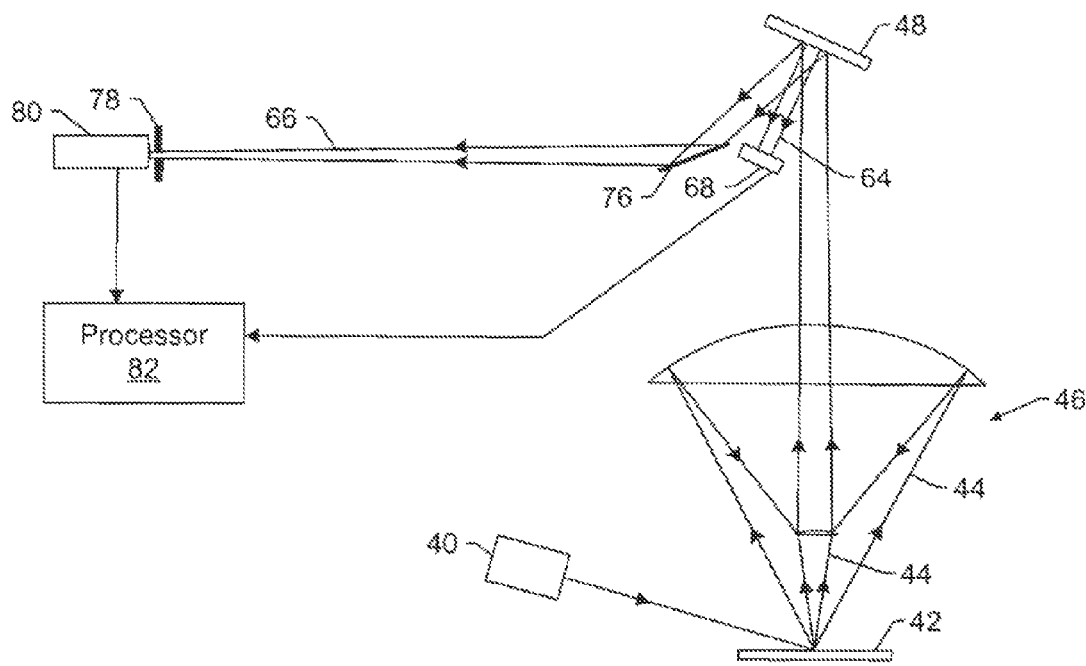
FIGS. 2, 2a, 3, and 3a are schematic diagrams illustrating side views of various embodiments of a system configured to inspect a substrate.

One embodiment of a system configured to inspect a substrate is shown in FIG. 2. The system includes illumination subsystem 40 configured to direct light to substrate 42. The substrate is typically rotated while the incident light beam is moved along the radial direction, hereby enabling to scan the whole surface in a spiral fashion. Other embodiments may include XY raster scan of the sample or the beam as an alternative to cover the surface to be inspected. The substrate may be a substrate such as that shown in FIG. 1 or any other substrate described herein. The light directed to the substrate may include any of the light described above. Illumination subsystem 40 may include any suitable light source(s) at different angle(s) of incidence and any other suitable optical component(s) such as filters, polarizers, etc. coupled to the light source(s).

The system shown in FIG. 2 is configured to separate light 44 scattered from the three interfaces described above. The system includes an objective configured to collect light scattered from the substrate. In addition, the system includes an optical element positioned in a path of the light collected by the objective. The optical element is configured to direct light scattered from the patterned features into a first direction and other scattered light into a second direction. For example, as shown in FIG. 2, reflective optical objective 46 directs the scattered light beam from substrate 42 onto optical element 48 that acts as a spatial light modulator or spatial filter.

In one embodiment, optical element 48 may be a micro mirror array (MMA) or liquid crystal on silicon. In this manner, the optical element may or may not be configured for articulation and/or actuation (movement) of individual elements of the optical element. For example, although the optical element may include an MMA that has individual mirrors capable of being moved, the optical element may include a static optical element that in of itself includes no moving parts (although the system may be capable of moving the static optical element (e.g., to switch out the optical element)). For example, the optical element may include a mirror and a static filter. In another example, the optical element may include a mirror and a static vignetting aperture or filter or a plurality of static apertures (e.g., rings of chrome-on-glass) configured to selectively block or redirect certain regions of the light incident on the optical element.

Figure 3:
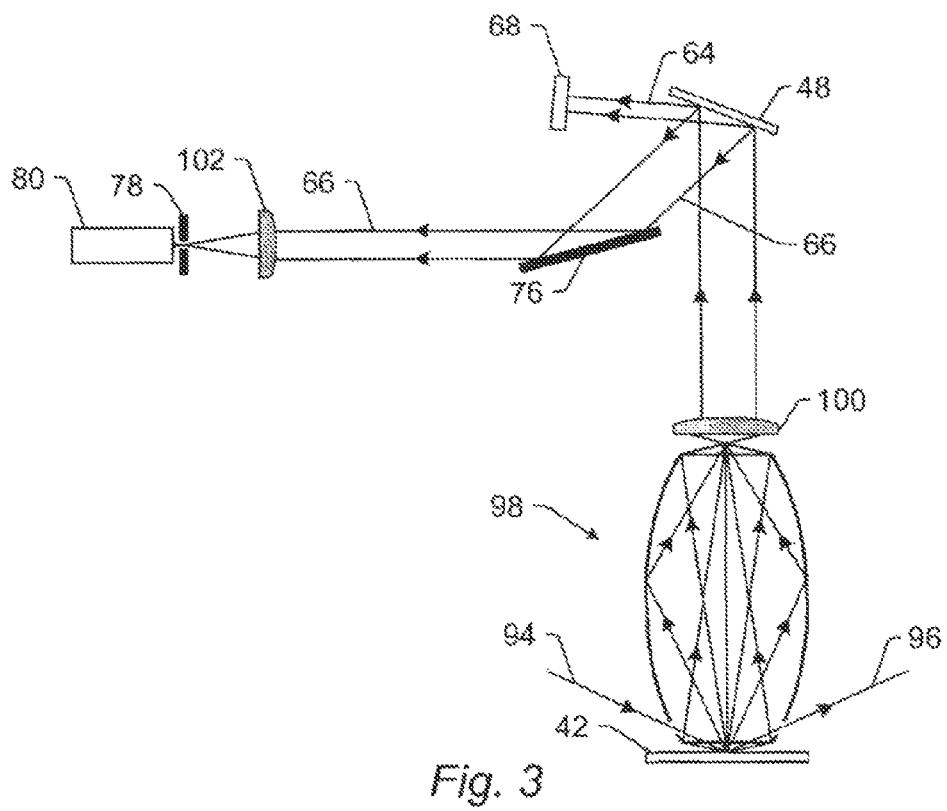
Figure 3A:
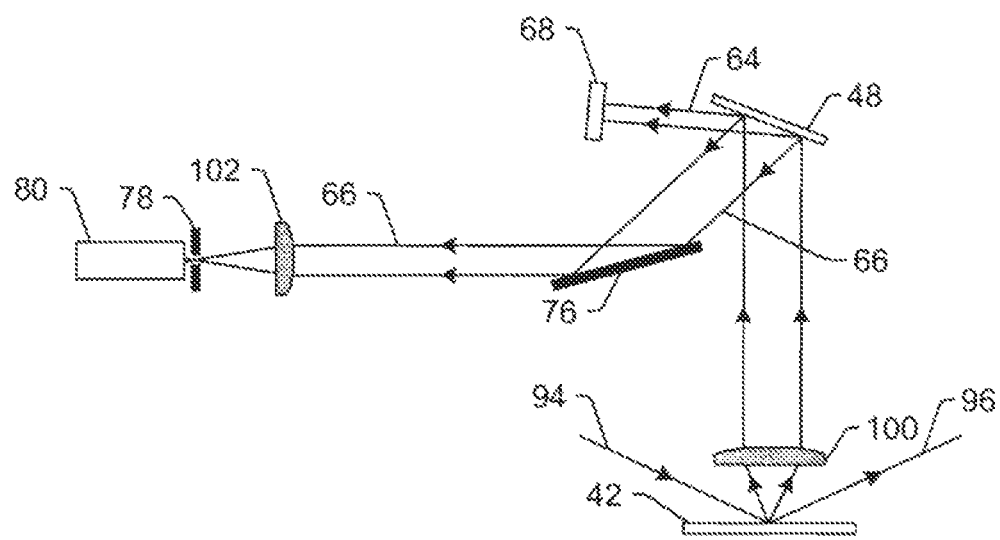

The optical element would ideally be placed at the reciprocal plane from the sample under test, i.e. at the Fourier or near-Fourier conjugate plane from the sample (e.g. one focal length above the objective in the case of the infinite conjugate embodiment shown in e.g. FIG. 3a), although it is to be noted that it will likely be more practical to place it further away and preserve functionality, as shown in most embodiments described herein.

Figure 4:
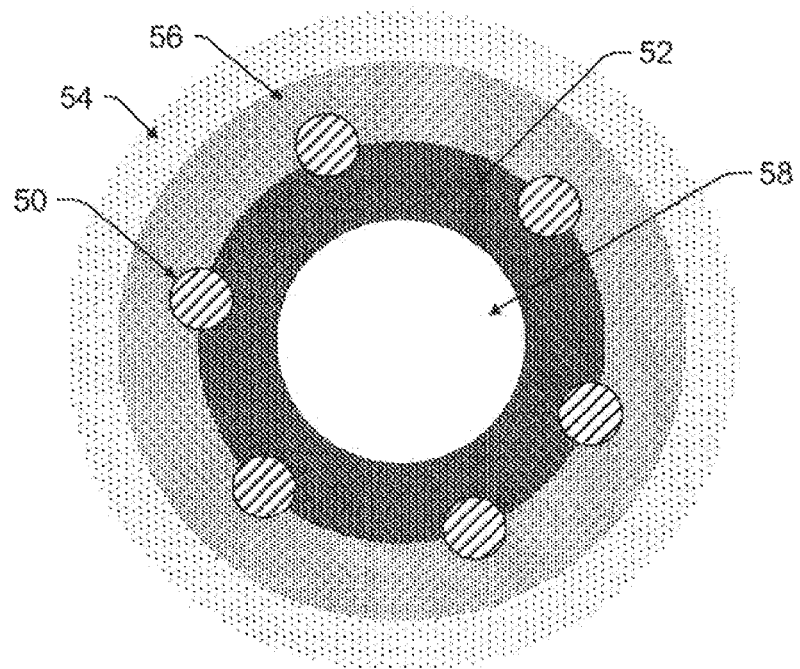
FIGS. 4-7 are schematic diagrams illustrating cross-sectional views of various scattered light from different portions of a patterned transparent substrate across an image plane of the systems described herein.

The scattered light from the ordered array of patterned features on the PSS produces a diffraction pattern that has the same symmetry as the hexagonal PSS pattern. At the output of the primary mirror of the reflective optical objective, the diffraction pattern of the PSS is superimposed upon the scatter from the GaN defects and the scatter from the bottom unpolished surface of the sapphire wafer. This is shown in FIG. 4 in which dots 50 are the diffraction orders (or diffraction pattern) from the PSS when illuminated by a normal incident beam and scattered light in region 52 is the scatter from the bottom surface of the sapphire. Scatter in region 54 is the scattered light from the top surface of the GaN, while scatter in region 56 is the scattered light from the bottom surface of the GaN. There is no scattered light collected in region 58 due to the configuration of the reflective objective shown in FIG. 2.

Figure 5:
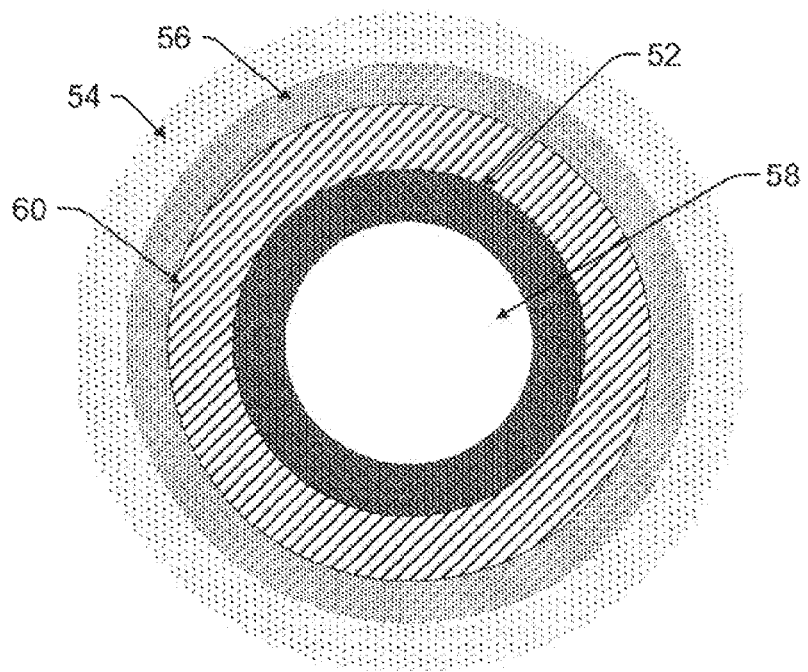
Figure 6:
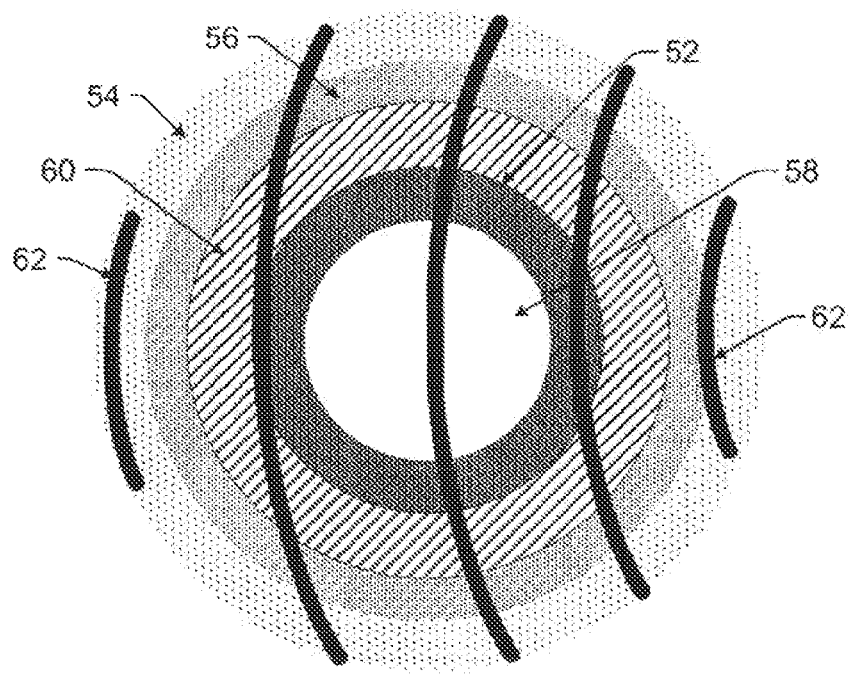

When the GaN-on-PSS wafer is rotated, the dots 50 of FIG. 4 also rotate, and the resulting diffraction pattern looks to the eye (or a slow camera) to be a ring as shown by ring 60 in FIG. 5 as the motion of the dots is blurred at slow enough integration times. As described above and shown in FIG. 1, the GaN-on-PSS may be illuminated by both a normal and an oblique beam. The oblique beam produces a diffraction pattern which is a series of arcs as shown in FIG. 6. More specifically, FIG. 6 shows the PSS-with-GaN scatter pattern at the output of the primary mirror with normal and oblique diffraction and top and bottom surface scatter. FIG. 6 shows the scatter from the GaN top and bottom surface in regions 54 and 56 respectively, the scatter from the back surface in region 52, the PSS diffraction from the normally incident beam with rotating substrate in region 60, and PSS diffraction from the obliquely incident beam with rotation as arcs 62.

Figure 7:
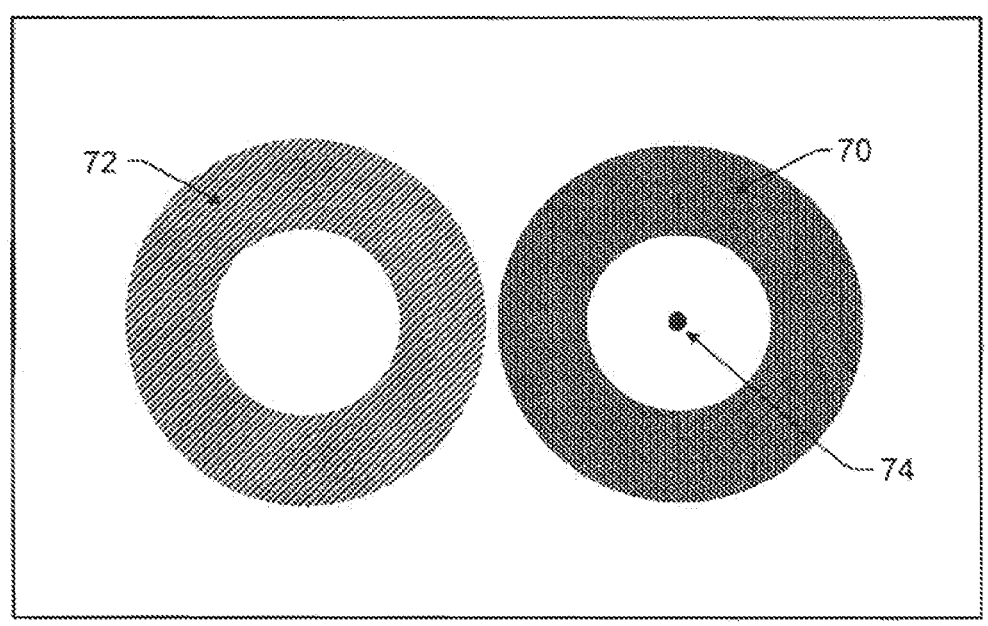

The diffraction patterns described above and any other diffraction patterns will be incident on the optical element and the optical element can be programmed to direct the PSS diffraction pattern out of the scattered light beam into a beam dump or detector as shown in FIG. 2. More specifically, the optical element is configured to direct light 64 scattered from the patterned features into a first direction (the rejected light path) and other scattered light 66 (the filtered scattered light beam) into a second direction. Light 64 scattered from the patterned features may be directed to element 68, which may be a beam dump or a detector (e.g., a camera) as described further herein. The other scattered light 66 is the scatter from the top surface of the GaN and the bottom surface scatter. This is shown, at the location of the field stop described further herein, in FIG. 7 where the bottom surface scatter from the normal beam is ring 70 and the bottom surface scatter from the oblique beam is ring 72 at the detector plane or at the image plane of the objective. The top surface scatter from the GaN due to both the normal and the oblique beams is represented by dot 74 at the center of ring 70.

The top surface scatter from the GaN can be separated from the bottom surface scatter by placing a field stop (e.g., a pinhole) just before the detector, as shown in FIG. 2. For example, as shown in FIG. 2, in one embodiment, the other scattered light may be directed by optical element 48 to reflective optical element 76 (e.g., a folding mirror or a turning mirror), which may direct the other scattered light through field stop 78 to detector 80. Detector 80 (e.g., a photomultiplier tube (PMT)) is configured to generate output responsive to only the light directed into the second direction. In addition, as described above, the PSS diffracted scatter pattern is removed by optical element 48 (e.g., the spatial filter) at the exit of the primary mirror.

The system also includes a processor configured to detect defects on the substrate using the output. For example, as shown in FIG. 2, the system may include processor 82 that is coupled to detector 80 such that the processor can receive the output generated by the detector. Processor 80 may detect the defects on the substrate using the output and any suitable algorithm and/or method to detect the defects. For example, the processor may apply a defect detection threshold to the output, and output above the threshold may be identified as defects or possible defects. The processor may be any suitable processor included in any suitable computer system known in the art.

The defects detected using the output generated by detector 80 will include other defects on the substrate. For example, in one embodiment, the substrate is transparent, the patterned features are formed on the upper surface after the upper surface is polished, a bottom surface of the substrate is not polished, and a transparent material is formed on the patterned features and the upper surface. Such a substrate may be further configured as described above. In such an embodiment, the system may include the spatial filter described above (e.g., field stop 78) that is positioned in a path of the other scattered light, and the spatial filter may be configured to block the light scattered from the bottom surface of the substrate and to transmit light scattered from an upper surface of the transparent material, the upper surface of the substrate, and defects on or in the transparent material and between the transparent material and the upper surface of the substrate. In this manner, in such an embodiment, the defects detected by the processor include defects on or in the transparent material and defects between the transparent material and the upper surface of the substrate and do not include defects on the bottom surface of the substrate.

However, the systems and methods described herein may be used for inspection of transparent substrates that do not have a transparent material formed thereon. For example, in another embodiment, the substrate is transparent, the patterned features are formed on the upper surface after the upper surface is polished, and a bottom surface of the substrate is not polished. In one such embodiment, the system includes a spatial filter (e.g., field stop 78), which may be configured as described above, positioned in a path of the other scattered light, and the spatial filter is configured to block light scattered from the bottom surface of the substrate and to transmit light scattered from the upper surface of the substrate and any defects on the upper surface of the substrate. In addition, in one such embodiment, the defects detected by the processor include defects on the upper surface of the substrate and do not include defects on the bottom surface of the substrate.

The systems and methods described herein may also be used for inspection of opaque substrates. For example, in one embodiment, the substrate is opaque (i.e., opaque to the illumination used by the inspection system), and the defects detected by the processor include defects on the upper surface of the substrate. In another embodiment, the substrate is opaque with transparent material formed on the substrate, and the defects detected by the processor include defects on or in the transparent material and defects between the transparent material and the upper surface of the opaque substrate In another embodiment, the systems described herein can be used for non-periodical/regular patterned samples to separate good from bad signals, e.g. by using the optical element as a low or high pass filter for the length scale of the defects of interest. In particular, there is a use case in which, using a static filter, defects of interest on GaN can be successfully separated from nuisance defects that are called "fish-scales" (because of their smoother shape) that have relatively low spatial frequencies. In this manner, the embodiments described herein can be used to eliminate the signal from patterned device features on the substrate or unwanted signal from any other "features" on the substrate.

In one embodiment, the system includes an additional detector configured to generate output responsive to only the light directed into the first direction. For example, as described above, element 68 may be a detector (e.g., a camera) configured to generate output responsive to only the light directed into the first direction. In one such embodiment, the processor is configured to use the output generated by the additional detector to determine diffraction from the patterned features and to adjust the optical element based on the diffraction to direct substantially all of the light scattered from the patterned features into the first direction and to direct any other undesirable scattered light into the first direction. For example, defects in the PSS pattern may pass through the spatial filter (e.g., the field stop) and will appear at the detector (e.g., a PMT). This is because the hexagonal symmetry of the PSS is broken by a missing or defective pattern bump or pit, and the scatter will not be filtered by the spatial light modulator. As a result, the PSS defect will appear at the detector (PMT). This pattern defect can be seen at the epi stage of the LED process since visible light used in inspection systems will penetrate through the GaN layer. A camera can be placed in the rejected light path of the spatial light modulator to view the diffraction from the PSS pattern and the scatter from various defects on the GaN epi. This camera image can be used to provide feedback for the adjustment of the spatial light modulator so as to optimize the rejection of undesired portions of the scatter pattern (e.g., the PSS diffraction or other nuisance defects). This camera can also be used to verify that the desired portions of the scatter pattern are being removed by the spatial light modulator. This would be accomplished by first using the spatial light modulator to direct the entire scatter pattern into the camera and then redirecting selected pixel regions to the PMT thereby eliminating undesired spatial frequencies from the detected signal.

In another such embodiment, the processor is configured to use the output generated by the additional detector to detect defects in the patterned features. In a further embodiment, the processor is configured to simultaneously detect the defects on the substrate using the output and use the output generated by the additional detector to detect defects in the patterned features. In some embodiments, the processor is configured to use the output generated by the additional detector to determine one or more characteristics of the patterned features. The one or more characteristics may include various metrology-like characteristics of the patterned features such as height, width, side wall angle and the like. In addition, the embodiments may be used to detect defects in the patterned features as described above and then in review mode the embodiments may be used to revisit locations on the substrate at which defects in the patterned features were detected such that the processor can use the output generated by the additional detector at those locations to determine more information about the patterned feature defects and/or determine a classification and/or root cause for the defects. In this manner, the embodiments may determine any issues with the patterned features in review mode.

Figure 2A:
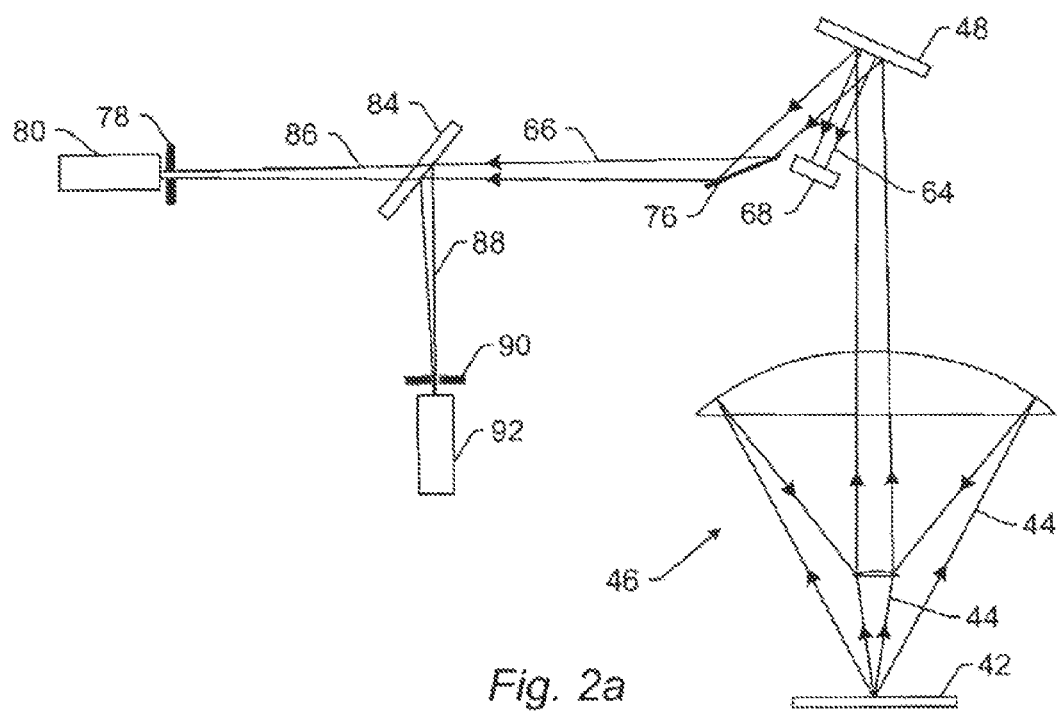

In one embodiment, the light directed to the substrate includes light having first and second discrete wavelengths, the first and second discrete wavelengths are directed to the substrate simultaneously at the same or different angles of incidence, the system includes a beam splitter configured to separate the other scattered light into first scattered light having the first wavelength and second scattered light having the second wavelength, and the system is configured such that the first and second scattered light is directed to different detectors simultaneously. This embodiment may be suitable to improve defect classification capability, based on the fact that two different incidence angles may be used simultaneously (one for each wavelength) and that the scattering signals differ for different incident angles as a function of the defect type (pits, particles, etc.). The beam splitter may include any suitable beam splitter known in the art. For example, as shown in FIG. 2a, the system may include beam splitter 84 that is configured to separate the other scattered light into first scattered light 86 having the first wavelength and second scattered light 88 having the second wavelength. As described above, first scattered light 86 may be directed through field stop 78 to detector 80. In a similar manner, second scattered light 88 may be directed through field stop 90 to detector 92. Field stop 90 and detector 92 may be configured as described above. The system shown in FIG. 2a may be further configured as described above.

In addition, it is possible to separate the different beams (e.g., red and violet beams) after the field stop field stop 78) by using a dichroic mirror, narrow band pass filters (not shown), and separate detectors (e.g., separate PMTs). Other potential embodiments would be to split different colors of scattered light with dichroic mirror(s) and direct each wavelength onto a separate optical element separate MMAs). After reflection from each optical element, the scattered beams would go through separate field stops to separate detectors (e.g., separate PMTs) for defect detection and classification. While having increased complexity and cost, the advantage of this embodiment is that each optical element can be optimized to reject the maximum signal from the PSS and pass the maximum signal from the defects.

FIG. 3 illustrates another embodiment of a system configured to inspect a substrate. This system includes an illumination subsystem (not shown in FIG. 3) that is configured to direct light 94 to substrate 42. Patterned features (not shown in FIG. 3) are formed on an upper surface of the substrate. The illumination subsystem may be further configured as described above. As a result of illumination of the substrate by the illumination subsystem, light 96 may be specularly reflected from the substrate. Light scattered from the substrate is collected by objective 98, which may be further configured as described above. Objective 98 may be an ellipsoidal mirror or a parabolic minor. The light collected by the objective may be transferred by refractive optical element 100 to optical element 48. Refractive optical element 100 may include, for example, a collimating lens. Optical element 48 may be configured as described above. Specifically, optical element 48 is positioned in a path of the light collected by the objective. In addition, the optical element is configured to direct light scattered from the patterned features into a first direction and other scattered light into a second direction. More specifically, the optical element is configured to direct light 64 scattered from the patterned features into a first direction (the rejected light path) and other scattered light 66 (the filtered scattered light beam) into a second direction. Light 64 scattered from the patterned features may be directed to element 68, which may be a beam dump or a detector (e.g., a camera) as described further herein. This other scattered light 66 is the scatter from the top surface of the GaN and the bottom surface scatter.

The top surface scatter from the GaN can be separated from the bottom surface scatter by placing a field stop (e.g., a pinhole) just before the detector, as shown in FIG. 3. For example, as shown in FIG. 3, in one embodiment, the other scattered light may be directed by optical element 48 to reflective optical element 76 (e.g., a folding mirror or a turning mirror), which may direct the other scattered light to refractive optical element 102, which focuses the scattered light through field stop 78 to detector 80. Detector 80 (e.g., a PMT) is configured to generate output responsive to only the light directed into the second direction. In addition, as described above, the PSS diffracted scatter pattern is removed by optical element 48 at the exit of the objective. The system shown in FIG. 3 may be further configured as described herein.

In another embodiment, the system shown in FIG. 3 may not include objective 98. For example, as shown in FIG. 3a, refractive optical element 100 may be configured to collect light scattered from the substrate and to transfer the collected light to optical element 48. The system shown in FIG. 3a may be further configured as described herein.

Another way to use the systems described above is to replace the optical element with a standard mirror and use a suitable plurality of detectors or a "detector array" (e.g., avalanche photodiode, PMT array, or photodiode array) in lieu of the MMA and discrete detector approach. When using a PMT array for instance, the scattered light beam from the collector is expanded so that it covers the entire PMT array. The PMT array is placed at a similar location as the MMA would be placed in the prior embodiment (Fourier or near-Fourier conjugate plane) and measures each segment simultaneously.

In most embodiments, if the system is configured to inspect another substrate in which patterned features are not formed, the optical element can be configured to direct all of the collected scattered light into the second direction so as to maximize the scattering light signal from defects on the substrate.

In an additional embodiment, the system is configured to inspect another substrate, patterned features are not formed on the other substrate, the system includes an additional detector configured to generate output responsive to only the light directed into the first direction, during review of defects detected on the other substrate, the optical element is configured to direct only a portion of the collected light into the first direction such that different portions of a differential scattering cross-section (DSC) from a defect can be sampled sequentially by the additional detector, and the processor is configured to use information about the DSC to classify the detected defect. In this manner, the optical element can be used for a detailed review or classification improvement of defects detected on the other substrate. In that mode, the incident light beam is stopped at a constant radius (track scan) or even at a constant position (on defect dwell), and the optical element is configured to direct only a portion of the collected light into the first direction such that different scattered radiation angles can be sampled sequentially by the additional detector, and the processor is then configured to use all the information collected (angle dependent scatter) to classify the detected defect. In this manner, the systems described herein may be used to identify defect types, as explained in more details just below.

In the semiconductor and other industries, to detect and classify the defects on a wafer is very critical. The ability to classify the defects allows to break down the raw defect counts into "defect count per defect type" statistics in the inspection report. This extra information typically allows better and tighter process control. When a tight beam is incident as a focused beam of light on a substrate with a defect (e.g., a particle, pit, bump, etc.), the scattered light in the entire upper hemisphere depends mostly on the following parameters: a) polarization, wavelength, and spot size of the incident light; b) angle of incidence with respect to substrate normal; and c) defect type (e.g., particle, pit, bump, etc.), size, geometry, and orientation (in axially asymmetric defects).

Figure 8:
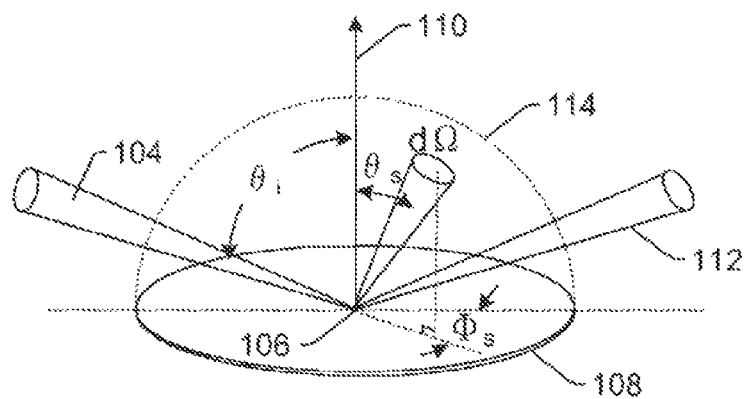
FIG. 8 is a schematic diagram illustrating a perspective view of one example of incident radiation and scatter definitions.

FIG. 8 shows incident light 104 and various scatter definitions, A focused beam of light 104 is incident on substrate 108 at an angle of incidence $\theta_i$ with respect to surface normal 110. The defect is located at origin 106 of this coordinate system. Reflected specular beam 112 is in the plane of incidence, which is defined by the plane which ID contains the incident beam and the surface normal. The defect scatters into the entire upper hemisphere 114. A small region of scattered intensity $d\Omega$, subtends at angle of $\theta_s$ to the surface normal. The azimuth angle $\phi_s$ is the angle between the projected $d\Omega$ on the substrate and the plane of incidence.

Figure 9A:
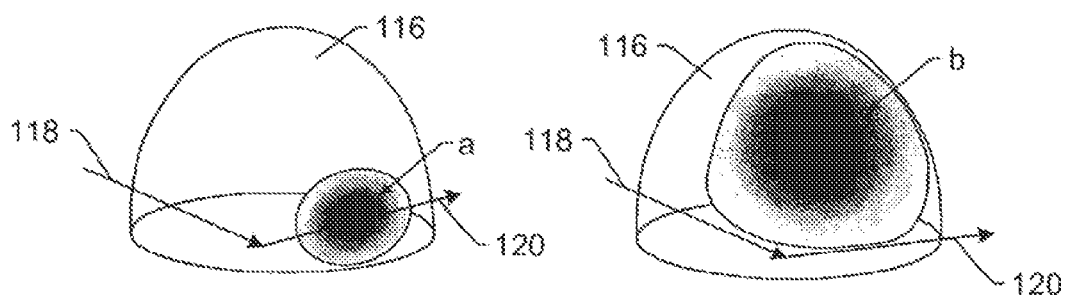
FIG. 9a is a schematic diagram illustrating a perspective view of different examples of scatter patterns from different defect types.

FIG. 9a shows the scatter pattern in upper hemisphere 116 produced by directing 405 nm wavelength light 118 onto a sapphire substrate at a 70 degree angle of incidence. FIG. 9a also shows the differential scattering cross-section pattern from a) a 600 nm polystyrene latex sphere and b) a 600 nm (lateral dimension) crystal oriented pit (COP). In addition, FIG. 9a shows specular beams 120 that would result from the illumination described above. In this manner, FIG. 9a shows the scatter intensity distribution for incident light (wavelength 405 nm), due to a particle and COP on a sapphire substrate. It is evident from the simulation results that the differential scattering cross-section (DSC) depends on the defect type.

Figure 9B:
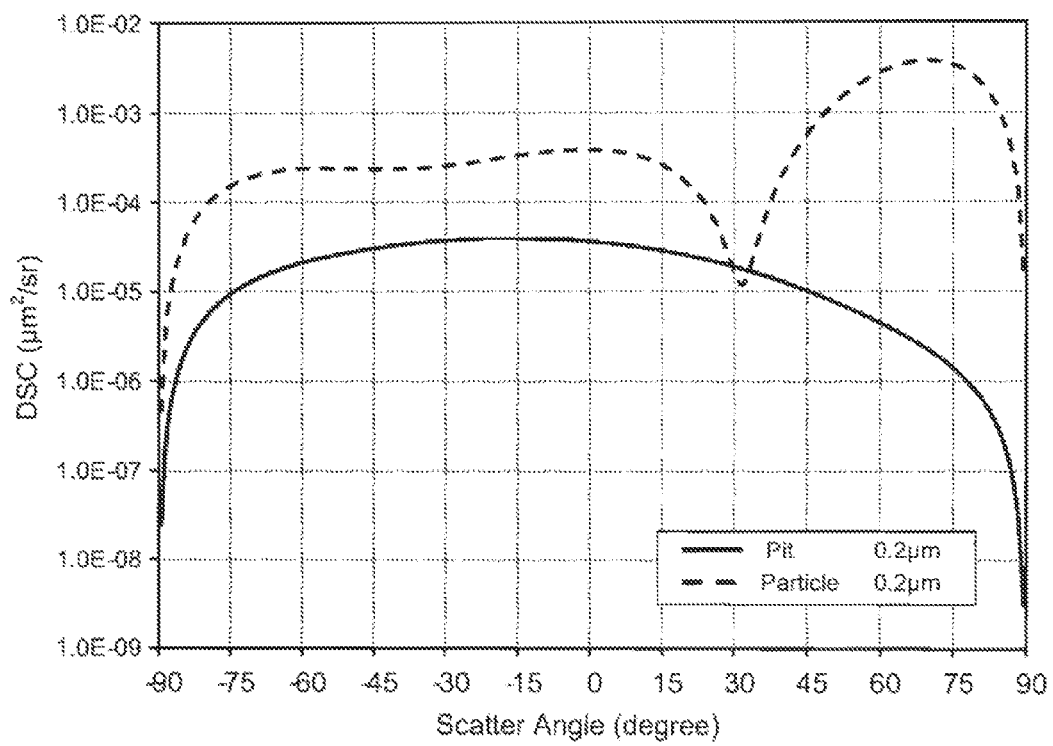
FIG. 9b is a plot showing differential scattering cross-section (DSC) for different defect types as a function of scatter angle.

FIG. 9*b* shows the simulated DSC versus scatter angle in the incident plane when 'P' polarized (where the electrical field vector is in the plane of incidence), 405 nut wavelength light is incident on a sapphire substrate (index of refraction n=1.786) at a 70° angle of incidence. The curves correspond to two different defect types on the sapphire substrate namely, a 200 nm diameter polystyrene latex sphere (n=1.59) and a 200 nm diameter COP with a 90° vertex angle. It is evident from these results that the DSC is dependent on the defect type.

Since each defect type has a unique DSC signature, accurately measuring DSC enables better defect classification. In the embodiments described herein, systems and methods are proposed to directly measure the DSC within a certain numerical aperture (NA) limited by the scatter collector (which could be a reflective or refractive microscope objective or an ellipsoidal scatter collector).

Figure 10:
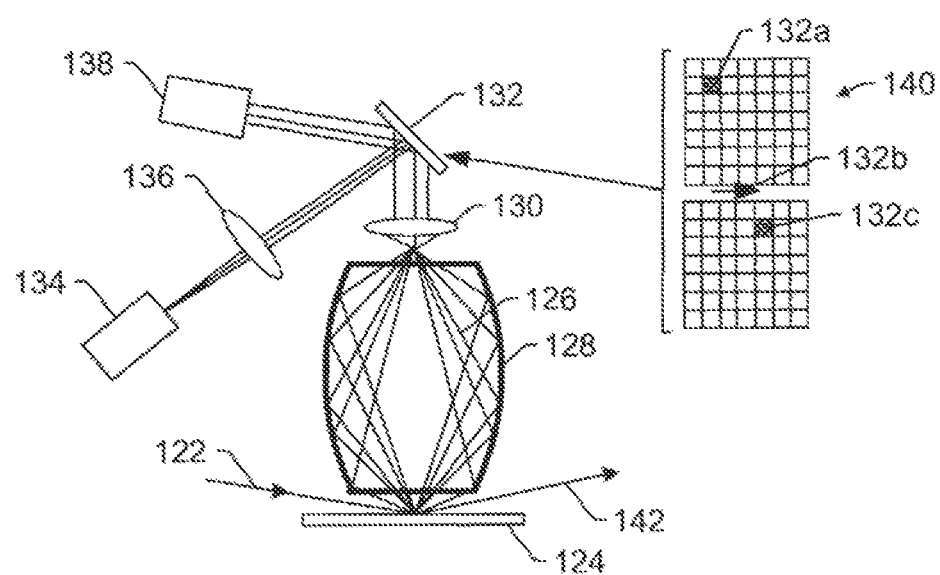
FIG. 10 is a schematic diagram illustrating a side view of one embodiment of a system configured to inspect a substrate.

FIG. 10 shows a system layout that can be used to measure the DSC using the optical element-based review method described above. The system includes a light source (not shown in FIG. 10) configured to direct focused beam of light 122 to the top of substrate 124 (e.g., a wafer surface). Scattered radiation 126 from a defect is collected using scatter collector 128 shown here as an ellipsoidal collector. The light from the scatter collector is collimated using collimating lens 130 and directed onto optical element 132 (e.g., a spatial light modulator). A MMA such as those commercially available from Texas Instruments may be used as the spatial light modulator. Each micro-mirror in the array can be individually controlled through software to be set at a +θ tilt state or a −θ tilt state. This ability to access and control individual mirrors enables creation of a "virtual pinhole" on the surface of the optical element by setting the micro-mirrors corresponding to the pinhole to a +θ tilt state while the rest of the micro-mirrors are set to −θ tilt state. For example, as shown in plan view 140 of the optical element, one mirror 132*a* can be set to one tilt state while all the other mirrors are set to a different tilt state. In addition, the optical element can be used to create a moving pinhole. For example, the mirrors can be individually and sequentially set to the first tilt state while all other mirrors are set to the different tilt state such that the pinhole essentially scans across the mirrors in direction 132*b*. In this manner, the pinhole can be moved from mirror 132*a* to mirror 132*c* and any other mirrors included in the optical element. In this manner, the system can create a moving pinhole on the optical element.

The light reflected from the pinhole zone falls on detector 134 (by being focused on the detector by focusing lens 136), which may be a PMT. At the same time, the light from the rest of the micro-mirrors is directed to another optical element 138, which may be a beam dump. Instead of a beam dump, another detector such as a camera can be used as described above for other embodiments. A fast photodetector, e.g., a PMT as shown, can also be used in some embodiments to monitor this rejected signal. Thus, the software controlled virtual pinhole that is formed on the optical element surface can be used to measure the two-dimensional DSC that is projected onto the optical element. Specularly reflected light beam 142 may also be collected and detected or simply directed to a beam dump (not shown). The system shown in FIG. 10 may be further configured as described herein.

The optical element can be operated in virtual pinhole (VP) mode or non-virtual pinhole (NVP) mode. During the NVP mode of operation, which may be used during defect detection, the entire optical element reflects the scattered light into the detector (e.g., the PMT), which enables the total integrated scatter (TIS) measurement. Once the defects have been detected, in order to review and identify the defect type, the system can then be operated in the VP mode. During this mode, the radiation is kept incident on the track or defect of interest (DOI) and DSC measurements can be made by sampling the DSC of the defect by virtual pinhole sampling. With this measurement, one is able to distinguish between a pit or a bump or a particle.

The entire optical element pattern can be refreshed for example at 5000 frames/second. Using, this frame refresh rate and 1024×768 extended video graphics adaptor (XVGA) mirror array, depending on the scattered light intensity per virtual pinhole, one can sample the entire DSC plane within approximately three minutes.

This would provide a very simple and elegant way to review the defects without much change to the basic optical setup.

An alternative way of operating the optical element is to divide (via software control) the optical element into an annular array or alternatively (for example) a 3 by 3 array, where each section of the array is switched together. Each section of the 3 by 3 array may contain hundreds of micro-mirrors, which are all switched together. The procedure for mapping the DSC would be to first direct one segment of the 3 by 3 array so that the scattered light falls into the path leading to the detector and the remaining 8 segments are directed to the beam dump. The segments are then switched during subsequent rotations of the wafer or disk so that each portion of the DSC is measured by the single detector. The disk or wafer may rotate many times during the measurement of a single segment of the DSC in order to average the signal. The time required to measure a single segment will still be substantially fast since a typical disk or wafer rotates at 5000 to 10,000 rotations per minute (RPM) during measurement. For example, suppose the optical element is divided into 9 segments and each segment is averaged for 10 rotations at 10,000 RPM. The total time required would be 0.54 seconds for the measurement of the DSC of a single defect. Of course, the optical element can be divided into more or fewer segments depending on the resolution with which it is desired to measure the DSC.

One way to use the systems described above would be to first direct the entire scattered light beam into the detector and then scan the entire disk or wafer. Once the defects have been located, one can identify the top ten or twenty defects and go back to those locations and measure the DSC. The DSC can then be used to classify these defects.

In one embodiment, the system is configured to inspect another substrate, patterned features are not formed on the other substrate, the system includes an additional detector array, the system is configured to replace the optical element with the additional detector array during review of defects detected on the other substrate such that different portions of a DSC from a defect can be sampled sequentially by the additional detector array, and the processor is configured to use information about the DSC to classify the detected defect. For example, another way to use the systems described above is to replace the optical element with a standard mirror and use a suitable plurality of detectors or a "detector array" (e.g., avalanche photodiode, PMT array, or photodiode array) in lieu of the MMA and discrete detector approach. When using a PMT array for instance, the scattered light beam from the collector is expanded so that it covers the entire PMT array. The PMT array is placed at a similar location as the MMA would be placed in the prior embodiment (Fourier or near-Fourier conjugate plane) and measures each segment simultaneously. The advantage of this method is speed as one may not have to stop the spiral scan to dwell at the defect location.

Another embodiment relates to another system configured to inspect a substrate. This system includes an illumination subsystem configured to direct light to the substrate, which may be configured as described above. Patterned features are formed on an upper surface of the substrate. In one embodiment, transparent material is formed on the patterned features and the upper surface of the substrate. However, transparent material may not be formed on the patterned features and the upper surface of the substrate. The system also includes an objective configured to collect light scattered from the substrate. The objective may be configured as described above. In addition, the system includes an optical element positioned in a path of the light collected by the objective. The optical element is configured to direct light scattered from the patterned features into a first direction and other scattered light into a second direction. The optical element may be further configured as described herein. The system further includes a first detector configured to generate output responsive to only the light directed into the second direction and a second detector configured to generate output responsive to only the light directed into the first direction. The first and second detectors may be further configured as described herein. In addition, the system includes a processor configured to detect defects in the patterned features or to determine one or more characteristics of the patterned features using the output generated by the second detector. By defects, we mean variations in the scatter signal for the patterned substrate from the normal scatter signal expected if the pattern was perfect. The processor may be further configured as described herein. The VP dwell method described above for a defect could be similarly used to review or better characterize a "pattern defect" and its specifics (side-wall angle dimension, pitch, anomalies).

This embodiment of the system may be further configured as described herein. For example, in one embodiment, the system is configured to inspect another substrate, patterned features are not formed on the other substrate, the system includes an additional detector array, the system is configured to replace the optical element with the additional detector array during review of defects detected on the other substrate such that different portions of a DSC from a defect can be sampled sequentially by the additional detector array, and the processor is configured to use information about the DSC to classify the detected defect. In another embodiment, the system is configured to inspect another substrate, patterned features are formed on the other substrate, the optical element is configured to direct only a portion of the collected light into the first direction such that different portions of a differential scattering cross-section from a pattern defect can be sampled sequentially by the second detector, and the processor is configured to use information about the differential scattering cross-section to determine one or more characteristics of the pattern defect. In a further embodiment, the system is configured to replace the optical element with an additional detector array such that different portions of a differential scattering cross-section from a pattern defect can be sampled by the additional detector array, and the processor is configured to use information about the differential scattering cross-section to determine one or more characteristics of the pattern defect. The system may be configured in this manner as described further herein.

An additional embodiment relates to another system configured to inspect a substrate. This system includes an illumination subsystem configured to direct light to the substrate, which may be configured as described above. Patterned features are not formed on an upper surface of the substrate. The system also includes an objective configured to collect light scattered from the substrate. The objective may be configured as described above. In addition, the system includes an optical element positioned in a path of the light collected by the objective. The optical element is configured to selectively direct the collected light into a first direction or a second direction. The optical element may be further configured as described herein. The system further includes a detector configured to generate output responsive to only the light directed into the second direction. The detector may be further configured as described herein. In addition, the system includes a processor configured to detect defects on the substrate using the output. The processor may be further configured as described herein. During inspection of the substrate, the optical element is configured to direct all of the collected light into the second direction. The optical element may be configured in this manner as described further herein.

In one embodiment, the system includes an additional detector configured to detect the light directed into the first direction. The additional detector may be configured as described above. During review of defects detected on the substrate, the optical element is configured to direct only a portion of the collected light into the first direction such that different portions of a DSC from a defect can be sampled sequentially by the additional detector. The optical element may be configured in this manner as described further above. In such an embodiment, the processor may be configured to use information about the differential scattering cross-section to classify the detected defect. The processor may be configured in this manner as described further herein.

In another embodiment, the system includes an additional detector array, the system is configured to replace the optical element with the additional detector array during review of defects detected on the other substrate such that different portions of a DSC from a defect can be sampled sequentially by the additional detector array, and the processor is configured to use information about the DSC to classify the detected defect. The system may be configured in this manner as described further herein. In an additional embodiment, during review of defects detected on the substrate, the substrate is stationary with respect to the system such that a DSC from a defect can be sampled multiple times sequentially. In other words, the system may be configured to dwell at a location on the substrate such that sufficient measurements of the DSC can be made. The system may be configured in this manner as described further herein.

Further modifications and alternative embodiments of various aspects of the invention may be apparent to those skilled in the art in view of this description. For example, various embodiments for substrate inspection are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a substrate, comprising:
an illumination subsystem configured to direct light to the substrate, wherein patterned features are formed on an upper surface of the substrate;

an objective configured to collect light scattered from the substrate;

an optical element positioned in a path of the light collected by the objective, wherein the optical element is configured to direct light scattered from the patterned features into a first direction and other scattered light into a second direction;

a detector configured to generate output responsive to only the light directed into the second direction;

an additional detector configured to generate output responsive to only the light directed into the first direction; and a processor configured to detect defects on the substrate using the output, wherein the processor is further configured to use the output generated by the additional detector to determine diffraction from the patterned features and to adjust the optical element based on the diffraction to direct substantially all of the light scattered from the patterned features into the first direction and to direct any other undesirable scattered light into the first direction.

2. The system of claim 1, wherein the optical element is a micro mirror array.

3. The system of claim 1, wherein the optical element is a static optical element.

4. The system of claim 1, wherein the substrate is transparent, wherein the patterned features are formed on the upper surface after the upper surface is polished, wherein a bottom surface of the substrate is not polished, and wherein a transparent material is formed on the patterned features and the upper surface.

5. The system of claim 4, further comprising a spatial filter positioned in a path of the other scattered light, wherein the spatial filter is configured to block light scattered from the bottom surface of the substrate and to transmit light scattered from an upper surface of the transparent material, the upper surface of the substrate, and defects on or in the transparent material and between the transparent material and the upper surface of the substrate.

6. The system of claim 4, wherein the defects detected by the processor comprise defects on or in the transparent material and defects between the transparent material and the upper surface of the substrate and do not include defects on the bottom surface of the substrate.

7. The system of claim 1, wherein the substrate is transparent, wherein the patterned features are formed on the upper surface after the upper surface is polished, and wherein a bottom surface of the substrate is not polished.

8. The system of claim 7, further comprising a spatial filter positioned in a path of the other scattered light, wherein the spatial filter is configured to block light scattered from the bottom surface of the substrate and to transmit light scattered from the upper surface of the substrate and any defects on the upper surface of the substrate.

9. The system of claim 7, wherein the defects detected by the processor comprise defects on the upper surface of the substrate and do not include defects on the bottom surface of the substrate.

10. The system of claim 1, wherein the substrate is opaque, and wherein the defects detected by the processor comprise defects on the upper surface of the substrate.

11. The system of claim 1, wherein the substrate is opaque with transparent material formed on the substrate, and wherein the defects detected by the processor comprise defects on or in the transparent material and defects between the transparent material and the upper surface of the opaque substrate.

12. The system of claim 1, wherein the processor is further configured to use the output generated by the additional detector to detect defects in the patterned features.

13. The system of claim 1, wherein the processor is further configured to simultaneously detect the defects on the substrate using the output and use the output generated by the additional detector to detect defects in the patterned features.

14. The system of claim 1, wherein the processor is further configured to use the output generated by the additional detector to determine one or more characteristics of the patterned features.

15. The system of claim 1, wherein the light directed to the substrate comprises light having first and second discrete wavelengths, wherein the first and second discrete wavelengths are directed to the substrate simultaneously at the same or different angles of incidences, wherein the system further comprises a beam splitter configured to separate the other scattered light into first scattered light having the first wavelength and second scattered light having the second wavelength, and wherein the system is configured such that the first and second scattered light is directed to different detectors simultaneously.

16. The system of claim 1, wherein the system is further configured to inspect another substrate, wherein patterned features are not formed on the other substrate, and wherein during inspection of the other substrate, the optical element is configured to direct all of the collected scattered light into the second direction.

17. The system of claim 1, wherein the system is further configured to inspect another substrate, wherein patterned features are not formed on the other substrate, wherein during review of defects detected on the other substrate, the optical element is configured to direct only a portion of the collected light into the first direction such that different portions of a differential scattering cross-section from a defect are sampled sequentially by the additional detector, and wherein the processor is further configured to use information about the differential scattering cross-section to classify the detected defect.

18. The system of claim 1, wherein the system is further configured to inspect another substrate, wherein patterned features are not formed on the other substrate, wherein the system further comprises an additional detector array, wherein the system is further configured to replace the optical element with the additional detector array during review of defects detected on the other substrate such that different portions of a differential scattering cross-section from a defect are sampled by the additional detector array, and wherein the processor is further configured to use information about the differential scattering cross-section to classify the detected defect.

19. A system configured to inspect a substrate, comprising:
an illumination subsystem configured to direct light to the substrate, wherein patterned features are formed on an upper surface of the substrate;

an objective configured to collect light scattered from the substrate;

an optical element positioned in a path of the light collected by the objective, wherein the optical element is configured to direct light scattered from the patterned features into a first direction and other scattered light into a second direction;

a first detector configured to generate output responsive to only the light directed into the second direction;

a second detector configured to generate output responsive to only the light directed into the first direction; and a processor configured to detect defects in the patterned features or to determine one or more characteristics of the patterned features using the output generated by the second detector, wherein the processor is further configured to use the output generated by the second detector to determine diffraction from the patterned features and to adjust the optical element based on the diffraction to direct substantially all of the light scattered from the attuned features into the first direction and to direct any other undesirable scattered light into the first direction.

20. The system of claim 19, wherein transparent material is formed on the patterned features and the upper surface of the substrate.

21. The system of claim 19, wherein the system is further configured to replace the optical element with an additional detector array to determine one or more characteristics of the patterned features using the output generated by the additional detector array.

22. The system of claim 19, wherein the optical element is further configured to direct only a portion of the collected light into the first direction such that different portions of a differential scattering cross-section from a pattern defect are sampled sequentially by the second detector, and wherein the processor is further configured to use information about the differential scattering cross-section to determine one or more characteristics of the pattern defect.

23. The system of claim 19, wherein the system is further configured to replace the optical element with an additional detector array such that different portions of a differential scattering cross-section from a pattern defect can are sampled by the additional detector array, and wherein the processor is further configured to use information about the differential scattering cross-section to determine one or more characteristics of the pattern defect.

24. A system configured to inspect a substrate, comprising:
an illumination subsystem configured to direct light to the substrate, wherein patterned features are not formed on an upper surface of the substrate;
an objective configured to collect light scattered from the substrate;
an optical element positioned in a path of the light collected by the objective, wherein the optical element is configured to selectively direct the collected light into a first direction or a second direction;
a detector configured to generate output responsive to only the light directed into the second direction; and
a processor configured to detect defects on the substrate using the output, wherein during inspection of the substrate, the optical element is configured to direct all of the collected light into the second direction, wherein during review of defects detected on the substrate, the substrate is stationary with respect to the system such that a differential scattering cross-section from a defect is sampled multiple times sequentially.

25. The system of claim 24, further comprising an additional detector configured to detect the light directed into the first direction, wherein during the review of defects detected on the substrate, the optical element is configured to direct only a portion of the collected light into the first direction such that different portions of the differential scattering cross-section from the defect are sampled sequentially by the additional detector, and wherein the processor is further configured to use information about the differential scattering cross-section to classify the detected defect.

26. The system of claim 24, further comprising an additional detector array, wherein the system is further configured to replace the optical element with the additional detector array during the review of defects detected on the substrate such that different portions of the differential scattering cross-section from the defect are sampled by the additional detector array, and wherein the processor is further configured to use information about the differential scattering cross-section to classify the detected defect.

* * * * *